US006314314B1

(12) United States Patent
Karp

(10) Patent No.: US 6,314,314 B1
(45) Date of Patent: Nov. 6, 2001

(54) METHOD FOR LOCATING AN INTERNAL BLEEDING SITE IN A HUMAN BODY

(76) Inventor: Seth J. Karp, 6 Ledgewood Rd., West Roxbury, MA (US) 02132

( * ) Notice: Subject to any disclaimer, the term of this patent is extended or adjusted under 35 U.S.C. 154(b) by 0 days.

(21) Appl. No.: 09/247,784

(22) Filed: Jan. 14, 1999

(51) Int. Cl.[7] .................................................... A61B 6/00
(52) U.S. Cl. ........................ 600/436; 424/1.11; 424/9.1; 424/9.4
(58) Field of Search .......................... 600/436; 424/1.11, 424/9.1, 9.4

(56) References Cited

U.S. PATENT DOCUMENTS

| | | | |
|---|---|---|---|
| 4,416,865 | * 11/1983 | Rhodes et al. | 924/1.1 |
| 4,418,052 | * 11/1983 | Wong | 424/1.1 |
| 4,427,646 | * 1/1984 | Olexa et al. | 424/1.1 |
| 4,455,290 | * 6/1984 | Olexa et al. | 424/1.1 |
| 4,773,430 | 9/1988 | Porath | 128/768 |
| 5,096,696 | 3/1992 | Galanakis | 424/1.1 |
| 5,217,705 | * 6/1993 | Reno et al. | 424/1.1 |
| 5,561,220 | 10/1996 | Dean et al. | 424/1.69 |
| 5,605,672 | 2/1997 | Bogdanov et al. | 424/1.65 |
| 5,620,675 | 4/1997 | McBride et al. | 424/1.69 |
| 5,645,815 | 7/1997 | Dean et al. | 424/1.69 |
| 5,659,013 | 8/1997 | Senger et al. | 530/350 |
| 5,707,603 | 1/1998 | Toner et al. | 424/1.41 |
| 5,792,742 | 8/1998 | Gold et al. | 514/2 |
| 5,849,260 | 12/1998 | Dean et al. | 424/1.69 |

OTHER PUBLICATIONS

Gjerloff Schmidt, K., et al. Scandinavian Journal of Gastroenteroloy (1986), 21, 407–414.
Alavi, A. Seminars in Nuclear Medicine (1982), vol.XII, No. 2, 126–138.
Palabrica, T.M. et al. Proceedings of the National Academy of Sciences (1989), vol. 86, 1036–1040.
Wasser, M.N.J.M., et al. Blood (1989), vol. 74, 708–714.
Williamson, M.R., et al. Radiology (1986), 159, 272–273.
Walker, K.Z., et al. European Journal of Nuclear Medicine (1990), 16, 787–794.
Oster, Z.H., et al. Proceedings of the National Academy of Sciences (1985), vol. 82, 3465–3468.

* cited by examiner

Primary Examiner—Marvin M. Lateef
Assistant Examiner—Eleni Mantis Mercader
(74) Attorney, Agent, or Firm—Weingarten, Schurgin, Gagnebin & Hayes LLP

(57) ABSTRACT

A technique for localizing an internal bleeding site in the human body is provided. The technique entails the injection of radioactively labelled protein or factor used in the clotting process in solution into a human body When the protein or factor has built up in sufficient quantities at a bleeding site to form a clot, the radioactive emission is used to detect the location of the clot. One or more passes of the detector can be used to accurately pinpoint the location of the clot, and thereby, locate the bleeding site.

9 Claims, 4 Drawing Sheets

METHOD FOR LOCATING AN INTERNAL BLEEDING SITE IN A HUMAN BODY

FIELD OF THE INVENTION

This invention relates to medical diagnostic techniques and more particularly to a technique for locating an internal bleeding site in a human body.

BACKGROUND OF THE INVENTION

Bleeding is a common reason for hospitalization and out-patient treatment, particularly in older individuals. Disease or trauma can cause a hemorrhage at virtually any location in the body. Bleeding through the skin is easily identified, since it is clearly visible. However, bleeding within an internal cavity or organ of the body can be much more difficult to identity. As such, critical treatment may delayed as time is spent attempting to localize the intern hemorrhage.

Internal bleeding is an important health problem. Approximately 1 in 5 people will experience at least one episode of significant internal bleeding during their lifetime About half of these episodes are due to bleeding from the colon. The most common cause of colonic bleeding is diverticulosis. Approximately sixty-five percent (65%) of persons develop this condition by age eighty-five. Fifteen percent (15%) of these people, or approximately ten percent (10%) of the entire population will experience significant bleeding as a result.

Many diagnostic techniques now exist to localize an area of internal hemorrhage. These techniques include endoscopy, angiography and nuclear medicine scans. Endoscopy involves the placing of an optical scope into a body orifice such as the esophagus stomach or large bowel. Once a bleeding site is visualized, treatment is often possible using well known techniques such as cauterization or banding. In general, this technique requires that active bleeding occur during the viewing procedure. Bleeding sites may be difficult to identify because of obscuration by blood and the fact that certain regions of the bowel and most internal organs are inaccessible to scopes.

Angiography is an invasive procedure involving the passage of a catheter into the patient's aorta through an entry site, usually in the leg. Dye is injected from the end of the catheter when the catheter is located adjacent to vessels in which bleeding is likely occurring. The dye pools in an area of active bleeding, producing a characteristic blush which can be seen using an X-ray camera. There are many disadvantages of this technique. The dye can cause reactions within the body which can cause kidney failure or even death. Serious bleeding can occur at the site through which the catheter is inserted, and at times this requires an operation to repair. In addition, high doses of X-rays are required to perform this test.

Finally, nuclear medicine scan involves the injection, into the patient's blood stream, of a radioactive marker which attaches to red blood cells. The cells are traced to an active bleeding site using remote scanners sensitive to radiation.

Note that each of the diagnostic tests described above require active bleeding to reveal the presence of an internal hemorrhage. It is often the case that by the time the diagnostic tests are performed, the clot produced by the body is successful at stopping the bleeding, so the test does not provide useful information. Without definitive treatment of the bleeding source about half of these patients will experience recurrent hemorrhage. This is a dangerous situation because the bleeding may occur at any time, even after the patient has left the hospital. The ability to localize the source would allow definitive treatment in many cases and greatly reduce the potential harm caused by bleeding. In cases of particularly severe hemorrhage, the inability to accurately localize a bleeding site may mean that the surgery required to correct it must be much larger in scale than would be required if the bleeding source were well known. The disadvantage to a larger operation are clear. It increases time and costs, increases complications and requires a longer recovery time. For example, if a patient has a life-threatening bleeding condition in the colon, inability to accurately define the region necessitates removal of the entire colon. Conversely, if localization were possible, the patient might lose only one quarter of the entire colon. The latter operation is shorter, simpler and the patient suffers no substantial disability following the operation.

Accordingly, it is an object of this invention to provide a method for localizing an internal bleeding site/hemorrhage that does not require substantial and invasive procedures or internal visible observations. This invention recognizes a consequence of the bleeding, the clot formed by the body at the site. This clot is produced during active bleeding and persists after the bleeding is stopped. This method should enable a bleeding site to be located regardless of whether the site is bleeding actively or is clotted. The method should allow localization with a high degree of accuracy under a variety of conditions.

SUMMARY OF THE INVENTION

This invention overcomes the disadvantages of the prior art by providing a method for localizing an internal bleeding site that relies upon the natural clotting process occurring at a bleeding site. By injecting one or more particular blood elements/proteins/factors involved in the clotting process that contains a radioactive trace element thereon, the clot will naturally accumulate a certain concentration of such proteins. Within a short period of time the concentration is sufficient to be detected by a standard radiation detector. A detector can be located in a radiological suite as a stand alone unit or as a hand-held Geiger counter. Multiple scans, taken from different angles, can provide a very exact location of the bleeding site. During an operation, the body can be surveyed internally with a sterile Geiger Counter to pinpoint the bleeding source. Proteins or factors involved in clotting that can be injected (and modified with a radioactive trace element) include platelets, Factors II, IIa, Va, VII, VIIa, IX, IXa, X, Xa, XI, XIa, XII, XIIa, XIIIa, fibrinogen, fibrin, fibronectin, von Willebrand's Factor, vinculin, vitronectin, Factor VIIIa and/or b component peptides, ADP, serotonin, platelet factor 4, bethathromboglobulin, high-molecular-weight, kinogen, prekallikrein and antithrombin III.

BRIEF DESCRIPTION OF THE DRAWINGS

The foregoing and other objects and advantages of the invention will become more clear with reference to the following detailed description as illustrated by the drawings in which.

DETAILED DESCRIPTION OF AN ILLUSTRATIVE EMBODIMENT

Figure 1:
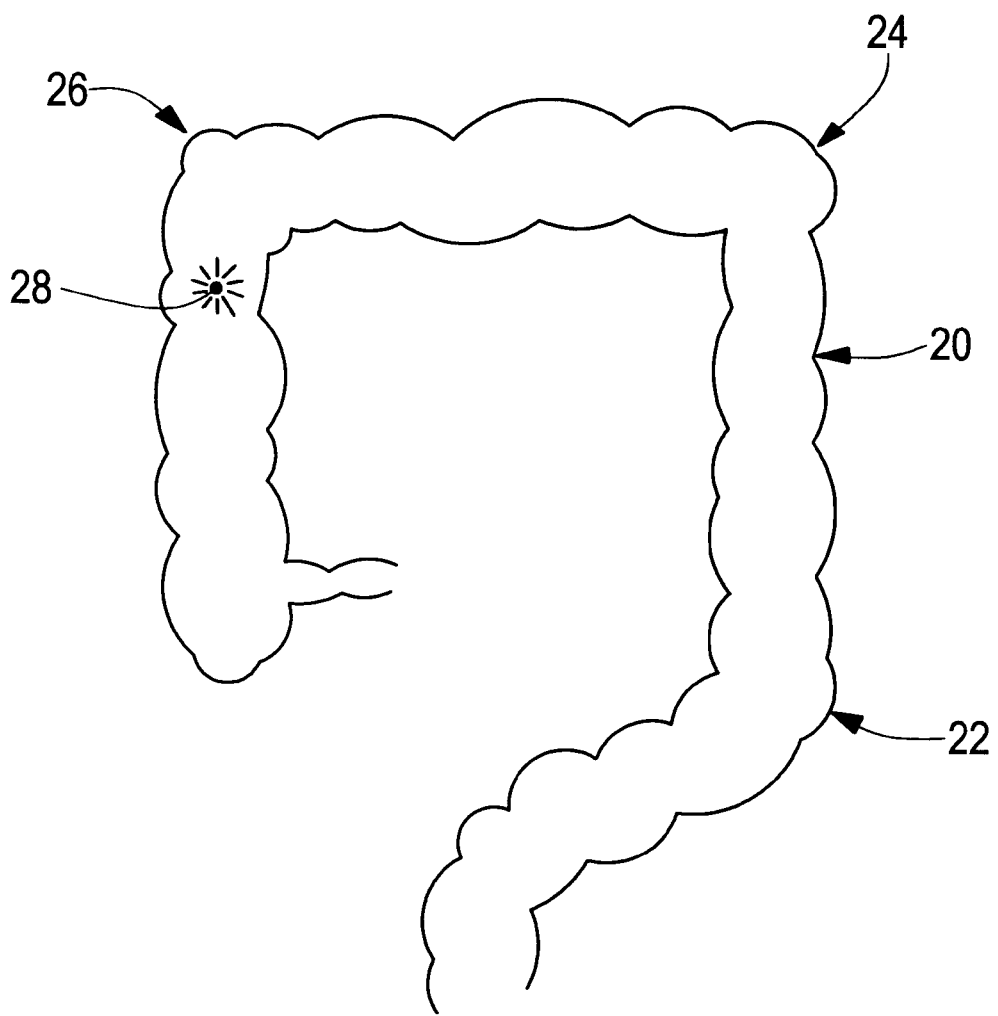
FIG. 1 is a schematic diagram of an exemplary bleeding site within a human colon.

FIG. 1 shows a human colon 20 including a series of characteristic bends 22, 24, and 26 with a bleeding site 28 located past the bend 24. Bleeding in this location would be typical for diverticulosis. Such a bleeding site would be difficult to locate using endoscopy because this site is relatively inaccessible to the scopes. Similarly, angiography and radioisotope often described fail to localize the bleeding.

Reference is now made to the coagulation cascade models that have been determined which govern the clotting of a bleeding site such as site 28 of FIG. 1. The most important mechanism that the body employs to stop bleeding is the formation of a clot Clots are composed of platelets and a number of specialized proteins. At the time of bleeding they collect at the site of a hemorrhage and a clot begins to form. Clotting is a dynamic process that involves initial platelet and protein deposition followed by a continuing deposition process and remodeling.

Bleeding occurs at the site of damage to the layer of cells which line blood vessels. This results in a hole in the vessel which allows the blood to escape. The body attempts to repair this hole in the following manner. Platelets and proteins in the blood stream are attracted to the damage by proteins produced by damaged cells and substances in the vessel wall which are exposed by the damage. These proteins and platelets begin the formation of a plug which will eventually grow to cover and repair the defect. Initially this plug is composed of proteins and platelets. This plug is temporary, and after the bleeding is successfully halted, a complex series of molecular events occurs which greatly increases the strength and durability of the plug and allows the cells underneath the clot to heal and reestablish the normal vessel.

Figure 3:
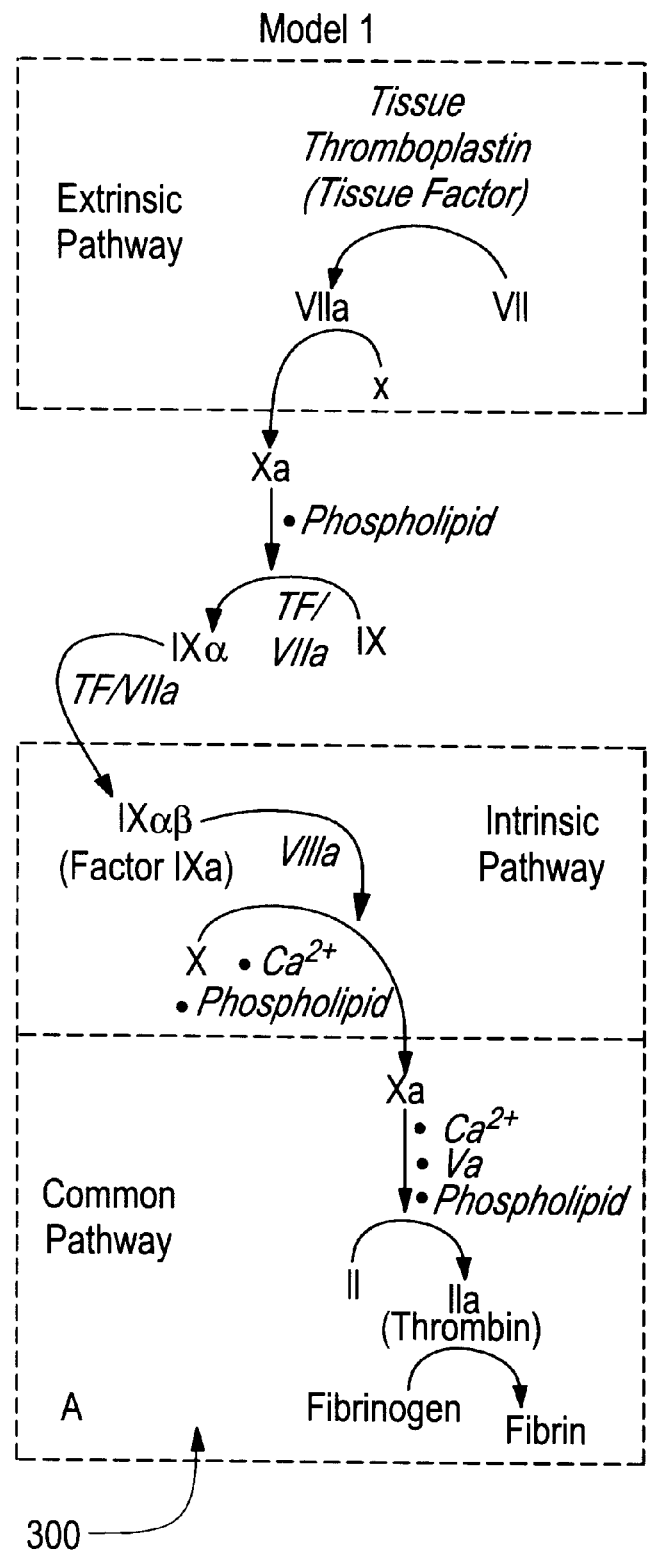
FIG. 3 is a flow diagram showing the blood coagulation cascade according to a first known model.
Figure 4:
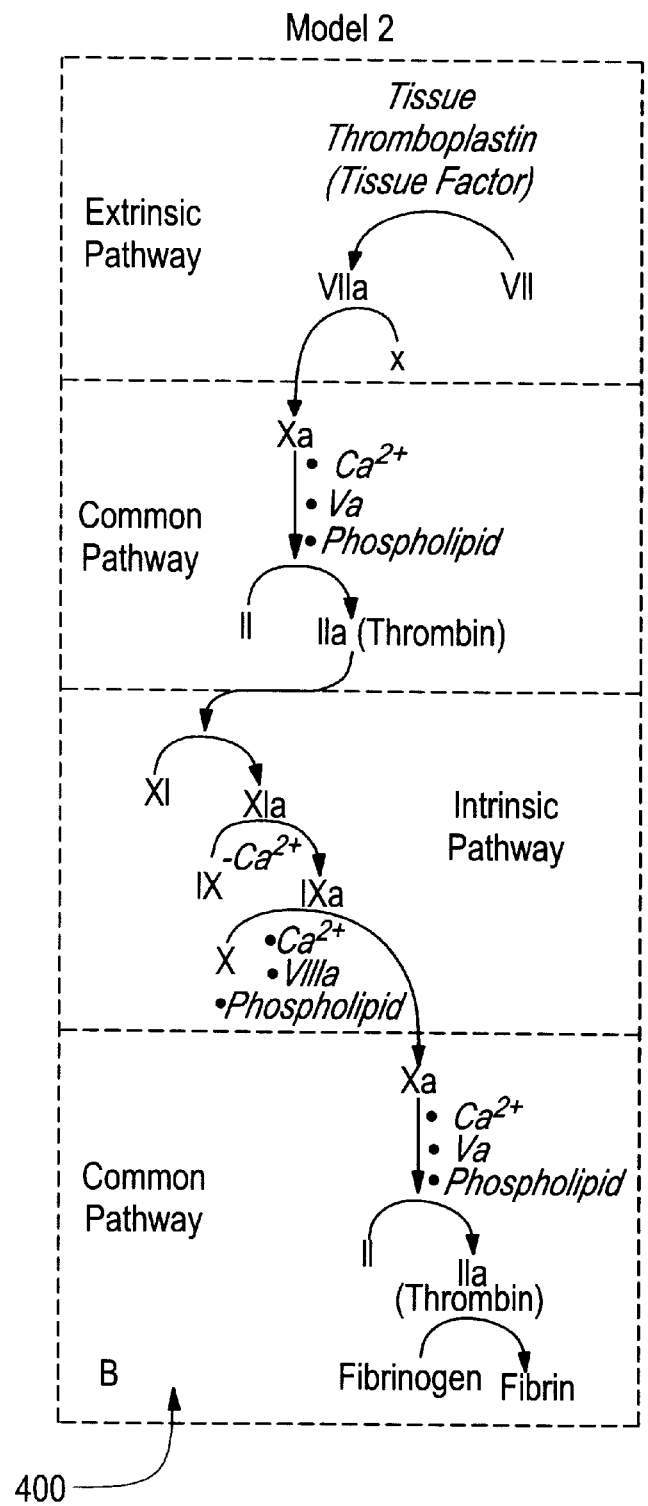
FIG. 4 is a flow diagram showing the blood coagulation cascade according to a second known model.

Historically, the molecules involved in clotting were divided into two distinct pathways, the intrinsic and extrinsic pathways. Recent work has shown there is considerable overlap between the two pathways and it is more useful to think of the pathways together. The precise details of the clotting cascade are not known, but the major aspects of is clotting are as follows. Damage to the blood vessel exposes tissue factor and other factors which cause platelets to adhere at the site. After a series of molecular events, activated factor VIIa and phospholipid convert factor IX to IXa and X to Xa. These molecules contribute to the production of thrombin (Factor II) from its precursor. Thrombin then converts fibrin to its active form. Fibrin is one of the principal proteins which make up the clot. This process of clot formation is a dynamic one, in which weaker areas of the clot may rupture, necessitating repeat of the process in a localized area. In this way, new molecules and platelets are constantly being recruited to the site of bleeding. At the final stage, activation of Factor XIII helps to cross link fibrin, which stabilizes the clot. Over time the fibrin molecules will link with each other in a dense mesh to form a durable clot. This clot will typically remain for a few days to weeks, depending on the size of the initial hemorrhage. The various factors recruited by the site from the blood stream to enable clotting are shown in FIGS. 3 and 4. The factors in each of the models 300 (FIG. 3) and 400 (FIG. 4) are combined with other elements in the bloodstream such as calcium and phospholipids to eventually form the final clotting products fibrinogen and fibrin. Even if full clotting does not occur, clotting material will be continuously deposited at the bleeding site. Because clotting material is virtually always present, this invention can use the presence of such material as the basis for detecting the exact location of the bleeding site. In general, most of the clotting factors will not be present in high concentration in portions of the body other than the actual bleeding site. By applying appropriate radioactive trace elements to one or more clotting factors shown in the coagulation cascade models 300 and 400 and FIGS. 3 and 4, a solution for detecting clotting can be produced.

Figure 2:
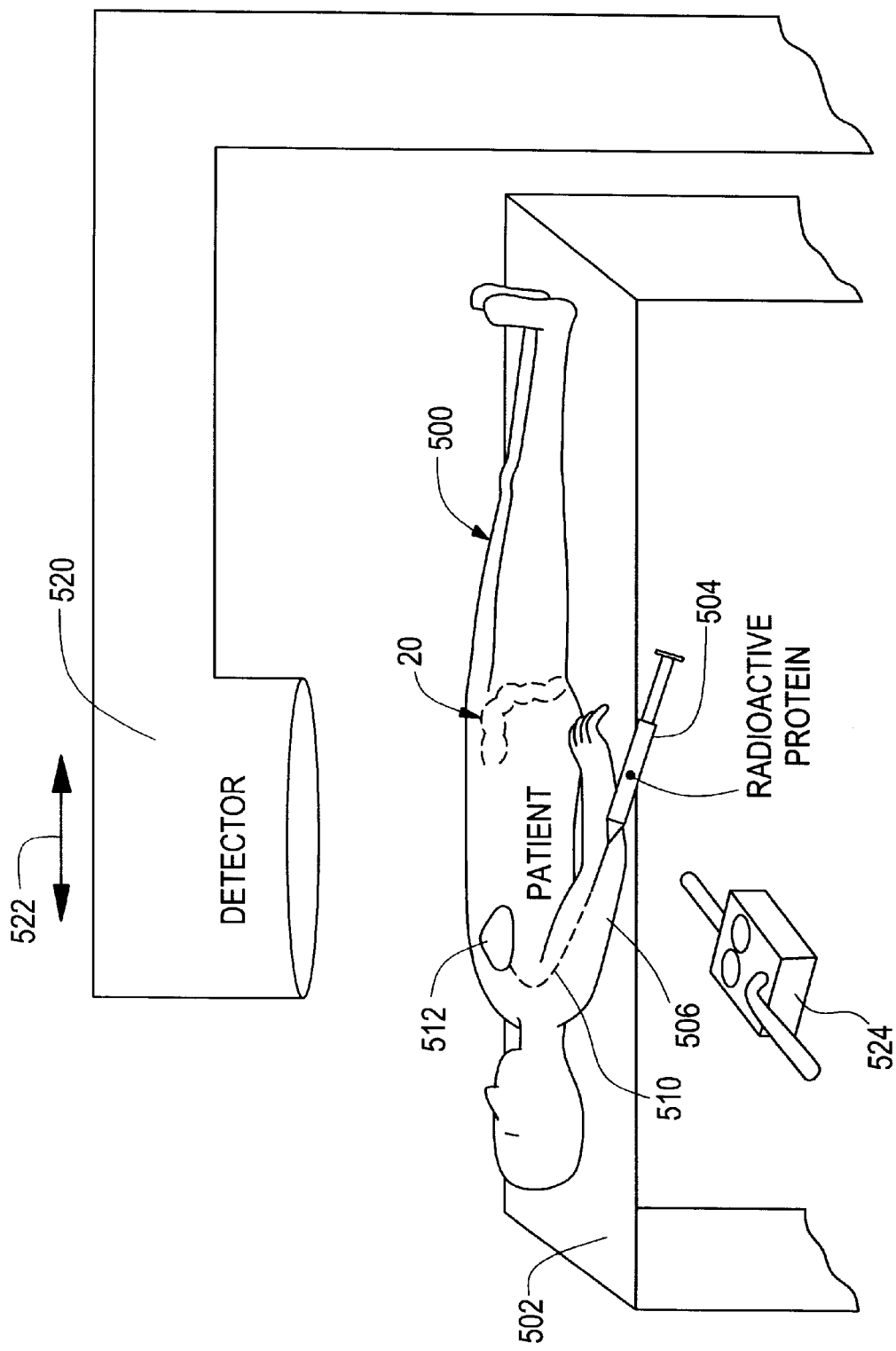
FIG. 2 is a schematic diagram showing the administration of the diagnostic procedure according to this invention.

With reference now to FIG. 2, a technique for administering factor or factors that enable detection of bleeding sites is shown. The patient 500 is shown reclining on a examination or operating room table 502. In some embodiments, the patient can be seated or even standing. A syringe 504 or other device for delivering an intravenous solution is applied to the patient's circulatory system shown here as a series of dotted lines 510 interconnected to the heart 512. Typically, a vein in the arm is used. The syringe, IV bag or other device carries the above-described platelets or proteins which can be one of several different clotting factors detailed in FIGS. 3 and 4. The platelets, factor or protein has a radioactive trace element such as (but not limited to) Technetium 99, Iodine 131, or Indium 111 that is attached to the protein or factor during manufacture according to well-known methods. For the purposes of this description the term "clotting factor" shall include platelets, as well as other materials that accumulate at a clotting site at some stage or stages during the clotting process. Platelets can be provided with a radioactive trace element using known techniques. For example the use of trace elememt indium 111 is described in an article of the Scandinavian Journal of Gastroenterology, May 21, 1986, page 407. The protein is provided in an aqueous solution that can include other elements such as saline. The trace protein or proteins/factors can be provided in concentrations of approximately one milligram per milliliter. Total volume of solution injected can be approximately 10–100 milliliters administered over a time period of approximately a few minutes. The protein/factor solution enters the bloodstream Through the circulatory system 510 and eventually migrates throughout the body until it finds its way to the bleeding site in the colon 20. Clotting is an ongoing process. The approximate time from administration of the solution to the build-up of a sufficiently detectable concentration is approximately a few minutes. At such time, a standard or customized detector 520 is located over the patient. If the approximate location of the bleeding site (the colon in this example) is known, then the detector can be immediately placed at this position. Otherwise, the detector is slowly moved over the entire patient (see arrow 522). The scanner can include rough focus and narrow focus so that an area can be first approximately localized and then pinpoint. The detector can also be moved over different portions of the affected area, once the approximate location is obtained. In this way, the exact location can be determined within the body. Other detectors have built-in multi-directional capabilities that require only one pass. Various existing nuclear medicine detectors can, for example, by employed. In addition, a hand-held detector 524 similar to an ordinary Geiger counter can be used. Each form of detector should enable the physician to pinpoint the location of the bleeding is based upon clot formation.

The following clotting factor or factors/proteins, alone and in combination, can be used in the aqueous solution according to this invention: Platelets, Factors II, Ia, Va, VII, VIIa, IX, IXa, Xa, XI, XIa, XII, XIIa, XIIIa, fibrinogen, fibrin, fibronectin, von Willebrand's Factor, vinculin, vitronectin, Factor VIIIa and/or b component peptides, ADP, serotonin, platelet factor 4, bethathromboglobulin, highmolecular-weight, kinogen, prekallikrein and antithrombin III. Other proteins used in the clotting process can also be used: in general, these proteins should have enough longevity in the clotting process, or should result in by-products that have enough longevity in the clotting process so they are not reabsorbed into the system too quickly. In addition, these proteins or factors should is not be deleterious to health when administered in a detectable concentration and should be present in clots at some time in sufficient concentrations to be detectable concentration by conventional devices. The proteins should remain sufficiently diluted in other parts of the body so that they do not trick the detector into giving a false reading. In other words, the protein should not have a substantial affinity for other organs or locations other than the clotting site. Also, the protein should exhibit sufficient build-up at the clotting site, in a reasonable short period of time, so that they are detectable over and background "noise" generated by remaining freely circulating radioactive proteins.

The foregoing has been a detailed description of a preferred embodiment. Various modification and additions can be made without departing from the spirit and scope of the invention. For example, the number and placement of scanners can be varied according to variety of well-known arrangements. The list of proteins used herein should not be taken as exhaustive. Additional proteins and other materials, each involved in various stages the clotting process, can be employed. In addition, the times and dosages used herein can be varied. For example, multiple administrations of radioactive trace proteins and/or different types of proteins in each administration can be employed. Accordingly, this description is meant to be taken only by way of example and not to otherwise limit the scope of the invention.

What is claimed is:

1. A method for localizing an internal bleeding site in the body of a mammal believed to be at risk of internal bleeding, said method comprising the steps of:

introducing into the circulatory system of said mammal a solution comprising a clotting factor that is capable of contributing to clot formation prior to the production of thrombin, said factor comprising a radioactive trace element;

permitting time to pass for at least some of the clotting factor in said solution to become localized to a site of bleeding to participate in clot formation;

scanning the exterior portion of the body of said mammal near a suspected said bleeding site with a detector that is sensitive to radiation; and externally detecting with a detector radiation emitted by said radiolabeled factor to determine a location of the bleeding site based upon a concentration of the radioactive trace element incorporated therein.

2. The method as set forth in claim 1 wherein the clotting factor is chosen from a list that includes platelets, Factors Va, VII, VIIa, IX, IXa, X, Xa, XI, XIa, XII, XIIa, XIIIa, von Willebrand's factor, vinculin, vitronectin, Factor VIIIa component peptides, Factor VIIIb component peptides, ADP, serotonin, platelet factor 4, betathromboglobulin, high-molecular weight, kinogen, prekallikrein and antithrombin III.

3. The method as set forth in claim 2 wherein the step of scanning includes positioning a Geiger counter over the bleeding site and determining therefrom the location of the bleeding site.

4. The method as set forth in claim 3 wherein the step of positioning includes moving the Geiger counter over multiple orientations adjacent the bleeding site to triangulate the position of the bleeding site.

5. The method as set forth in claim 4 wherein the bleeding site is located in the colon.

6. The method as set forth in claim 3 wherein the step of positioning includes locating a stationary radiation detector with respect to the bleeding site.

7. The method as set forth in claim 3 wherein the step of positioning includes moving a handheld radiation detector over an area of a body containing the bleeding site.

8. A method for localizing an internal bleeding site in the body of a mammal believed to be at risk of internal bleeding, said method comprising the steps of:

introducing into the circulatory system of said mammal a solution comprising a clotting factor that is capable of contributing to clot formation, said factor comprising a radioactive trace element;

permitting time to pass for at least some of the clotting factor in said solution to become localized to a site of bleeding to participate in clot formation;

scanning the exterior portion of the torso of said mammal near a suspected said bleeding site with a detector that is sensitive to radiation; and externally detecting with a detector radiation emitted by said radiolabeled factor to determine a location of the bleeding site based upon a concentration of the radioactive trace element therein.

9. The method of claim 8, wherein said suspected bleeding site is in the colon.

* * * * *